United States Patent [19]

Nishioka

[11] Patent Number: 5,318,679
[45] Date of Patent: Jun. 7, 1994

[54] SYNTHESIS OF CHAIN CHEMICAL COMPOUNDS

[75] Inventor: Gary M. Nishioka, Pataskala, Ohio
[73] Assignee: H & N Instruments, Inc., Newark, Ohio
[21] Appl. No.: 8,131
[22] Filed: Jan. 25, 1993

Related U.S. Application Data

[63] Continuation-in-part of Ser. No. 741,771, Aug. 7, 1991, abandoned.
[51] Int. Cl.$^5$ .............................................. C07K 1/00
[52] U.S. Cl. .......................... 204/157.68; 204/157.61; 436/518
[58] Field of Search ...................... 204/157.61, 157.68; 372/15, 25; 436/518

[56] References Cited

U.S. PATENT DOCUMENTS

| | | | |
|---|---|---|---|
| 4,704,583 | 11/1987 | Gould | 330/4.3 |
| 4,746,201 | 5/1988 | Gould | 350/394 |
| 5,143,854 | 9/1992 | Pirrung et al. | 436/518 |

OTHER PUBLICATIONS

"Lights! Camera! Print it! Laser Printer Technology Explained" Alfred Poor (PC Magazine, Nov. 14, 1989, pp. 168–169).
"Light-Directed, Spatially Addressable Parallel Chemical Synthesis" S. Fodor et al., Science, 251, 767 (1991).
A. Patchornik et al., JACS, 92, 6333 (1970) "Photosensitive Protecting Groups".
"Photoremovable Protecting Groups in Organic Synthesis" V. N. Pillai, Synthesis, 1 (1980).
"Binding activities of a repertoire of single immunoglobulin variable domains secreted from *Escherichia coli*" E. S. Ward, et al., Nature, vol. 341, 544 (1989).
"Peptides, Structure and Function" edited by C. M. Deber, V. J. Hruby, and K. D. Kopple, Pierce Chemical Co., Rockford, Ill., (1985).
"Searching for Peptide Ligands with an Epitope Library" J. K. Scott and G. P. Smith, Science, vol. 249, 386 (1990).
"Random Peptide Libraries: A Source of Specific Protein Binding Molecules" J. J. Devlin, L. C. Panganiban, and P. E. Devlin, Science, vol. 249, 404 (1990).
"Laser Recording And Image-Quality Evaluation" K. Minoura, et al., SPIE, vol. 1254, 24 (1990).
"A laser scanning optical system for high-resolution laser printer" T. Maruyama, et al., SPIE, vol. 1254, 54 (1990).
"Immunogenicity of Synthetic Peptides Corresponding to Flexible and Antibody-accessible Segments of Mouse Lactate Dehydrogenase (LDH)-$C_4$*" H. Hogrefe, P. Kaumaya, and E. Goldberg, J. Biol. Chem., vol. 264, 10513 (1989).
"Peptide engineering of protein topographic determinants for vaccines" P. Kaumaya, et al., in "Peptides 1990", ESCOM Science B.V. (1991).
"Synthesis and Biophysical Characterization of Engineered Topographic Immunogenic Determinants with aa Topology" P. Kaumaya, et al., Biochemistry, 29, 13 (1990).
"Single-Domain Antibodies Promise New Chemical, Medical Applications" C&E News, Nov. 20, 1989.

*Primary Examiner*—John Niebling
*Assistant Examiner*—Cybille Delacroix-Muirheid
*Attorney, Agent, or Firm*—Sidney W. Millard

[57] ABSTRACT

The present invention is an improved method of making sequenced chemical chain compounds through the application of laser copy technology to UV light directed spatially addressed parallel chemical synthesis and is particularly useful in the production of numerous proteins of varying amino acid sequences on a restricted solid support. Chemical groups, such as amines, are attached to the surface of a solid sup- port, such as flat glass, and subjected to chemical reaction disposed to link chemical units to the attached groups that are protected from further reaction by photolabile groups. Such solid support and photolabile protected units are then selectively deprotected by irradiation with a UV laser beam. The support and attached units are then subjected to chemical reaction to link chemical units to the selectively deprotected units. By repeated such treatment it is possible to produce unlimited combinations of chain chemical units in less time and at greater efficiency than has previously been possible.

12 Claims, 1 Drawing Sheet

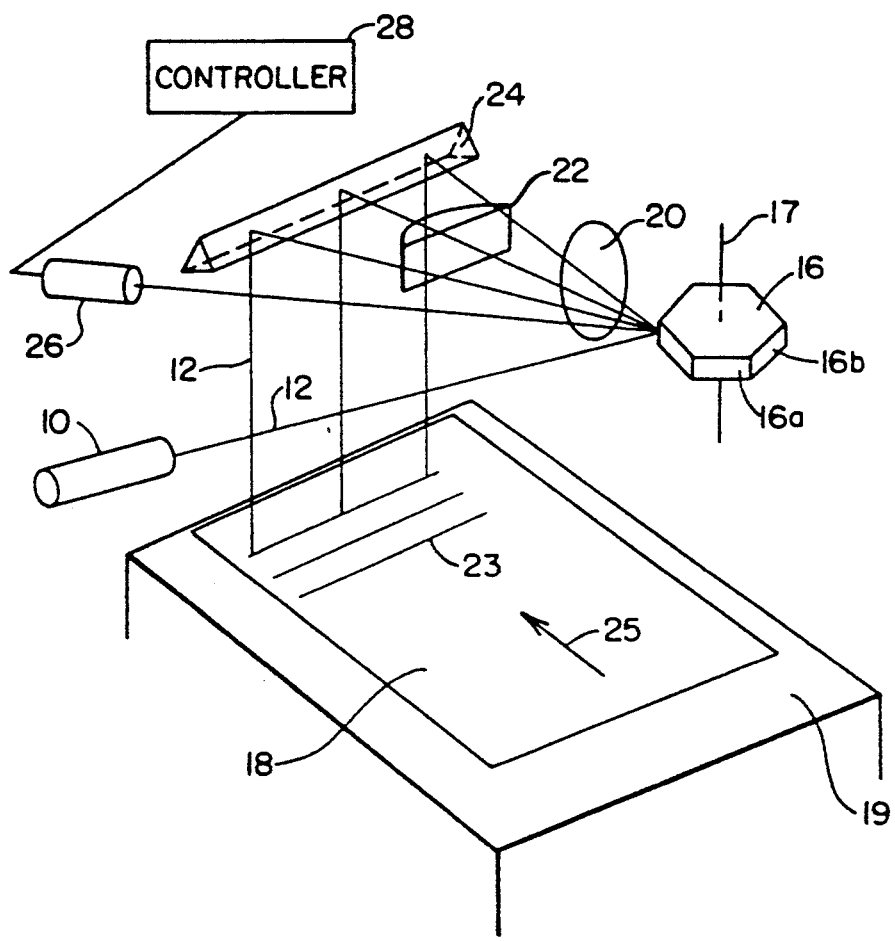

SYNTHESIS OF CHAIN CHEMICAL COMPOUNDS

This is a continuation-in-part of application Ser. No. 07/741,771, filed Aug. 7, 1991, now abandoned.

FIELD OF THE INVENTION

The present invention is an improved method of making sequenced chemical compounds through the application of laser printing technology to light directed spatially addressed parallel chemical synthesis.

BACKGROUND OF THE INVENTION

Chemicals of sequenced units, such as proteins which are composed of sequences of amino acids may be produced by solid phase chemistry wherein chemical units attached to a solid support are reacted with chemicals that attach other selected units to the units attached to the solid support to form unit chain compounds. Such two unit compounds may then be treated with the same or other chemicals repeatedly to form any predetermined number of units of sequenced compounds.

By providing photolabile protecting groups to the exposed units and sequentially unmasking certain areas of such units by light irradiation and exposing such unprotected areas to a reactive chemical disposed to attach a desired unit to the exposed units it is possible to create two unit chains in a confined area of the support. By repeating such steps in the same or other areas of the support and repeating varying chemical treatments as set forth above it may be readily seen that numerous differing chemical chain compounds may be effected in a confined space on a single support.

This technology is of particular significance in the biological production of antibodies with sequences of amino acid units that will exhibit a high level of binding and specificity for a protein. The binding of an antibody to a specific antigen is critically important in biological systems, since the specificity and strength of the antibody-antigen interaction is crucial to the operation of the immune system. The specificity of an antibody for a protein has been traced to highly variable segments in the antibody chain generally consisting of 6 to 10 amino acid sequences. It has been found that antibody segments containing one highly variable sequence, called a domain, exhibit high levels of binding and specificity for a protein ("Single-Domain Antibodies Promise New Chemical, Medical Applications" C&E News, Nov. 20, 1989).

The determination of the set of polypeptides that bind specifically to any given protein would be of obvious use in a variety of therapeutic and diagnostic treatments. Brute force determination of the sequences has been thought of as all but impossible. There are 20 common amino acids, so the number of possible 6 member polypeptides is $20^6$, or 64 million.

A recent development has shown promise in determining these sequences, through the synthesis of large numbers of peptides bound to a solid support. This method combines techniques of solid phase peptide synthesis, photolabile protecting groups, and photolithography to achieve light directed, spatially addressable parallel chemical synthesis. The method works as follows. A solid support (typically a glass microscope slide) is reacted with aminopropyltrie-thoxysilane to form amine groups on its surface. These groups are then reacted with an amino acid whose amine function is protected by a photolabile protecting group. The surface is then masked, for example, the surface is everywhere covered except for a rectangular strip exposing 5% of the exposed surface. The surface is then irradiated with UV light, activating only 5% of the exposed surface. The surface is then reacted with an amino acid whose amine function is also protected by a photolabile group; only the activated portion of the surface reacts with the amino acid. The masking, irradiation, and reaction step is repeated, with a different area exposed and a different amino acid reacted with the surface. After 20 steps, 20 parallel strips exist on the surface, each strip containing a different amino acid bound to the surface.

This process is then repeated, but with masks rotated to a position perpendicular to those used in the first masking sequence. At the end of the process all possible two member polypeptides have been synthesized on the solid support. Each polypeptide combination is located in squares formed from the intersection of the strips. The above procedure may be repeated to achieve any number of differing amino chain combinations in such intersecting squares.

This method has been used to prepare 1,024 different polypeptides on a square centimeter of surface. Utilizing the method of the present invention the potential exists for the synthesis of millions of polypeptides bound on a solid support. This method has also been used to synthesize different oligonucleotides on a solid support.

SUMMARY OF THE INVENTION

The present invention is the discovery that significantly improved deprotection of photolabile protected chemical units attached to a solid support can be achieved by scanning such units with ultra violet laser beams using laser printing techniques. Higher density yields of synthesis sites at less time are obtained over conventional irradiation techniques including non-printing laser techniques. It is possible to employ programmable deprotection schemes when utilizing such beams by applying laser printing techniques. Also, the use of laser printing techniques offers a much simpler and convenient means for deprotecting such reactants over the conventional masking and exposure techniques.

It is accordingly an object of the present invention to provide a laser beam to deprotect photolabile protected reactive chemical units attached to a solid support.

It is also an object of the present invention to scan photolabile protected reactive chemical units attached to a flat solid support with a UV laser beam printer.

A further object of the present invention is to apply programmable deprotection schemes to photolabile protected chemically reactive units attached to a support through the use of laser copy technology.

A still further object of the present invention is to provide an enhanced means for determining the set of polypeptides that bind specifically to a given protein through the synthesis of large numbers of peptides bound to a solid support.

BRIEF DESCRIPTION OF THE DRAWING

The figure is a schematic representation of a laser engine which may be used to accomplish the method of the present invention.

DETAILED DESCRIPTION OF THE INVENTION

Particularly desirable means for controlling the spatial coordinates of a laser beam is accomplished by the apparatus depicted by the drawing. A UV beam source 10 generates ultra violet beam 12 which reflects from the surfaces of a rotating mirror 16 and onto the surface of a glass support 18 that is seated on a precision translator 19.

The surface of glass support 18 has been provided with attached chemical units (not shown) that have been provided with photolabile protecting groups. Mirror 16 is many sided (octagonal etc.) being composed of multiple flat surfaces (illustrated at 16a, 16b etc.). Each such surface upon rotation is disposed to reflect laser beam 12 onto the surface of support 18 through focusing lens 20, curvature compensating lens 22 and reflecting mirror 24 when facing the beam. By rotating the mirror 16 about its axis 17, as each flat surface 16a, 16b, etc. sequentially faces beam 12, the beam is swept across the surface of support 18 and its coating of photolabile protected units deprotecting such units along the scan lines 23. By incrementally advancing the support 18 in the direction of the arrow 25 between each scan by each of the mirrors during rotation a series of scan lines 23 (deprotected areas) is achieved. The result is a support having multiple scan lines of deprotected chemical units which may then be reacted with chemicals to add new optionally different chemical units which may also be protected by photolabile groups. Individual scan lines may be selectively rescanned with beam 12 for subsequent additions of varying chemical units to provide controlled yields of chain compounds of unlimited differing chain units.

Further, support 18 may be rotated and rescanned with beam 12 to provide intersecting scan areas and multiple chain units as described above in respect to the conventional masking techniques.

Preferred control of the spatial coordinates of the laser beam deprotection of the units is achieved by employing a shutter (not shown) to block the beam surface when desired. A resulting pulsed beam enables one to build grids with points or restricted areas of deprotection substantially increasing the number of polypeptides that can be created on a single substrata or in a space of a few square micrometers.

Although adequate pulsating laser beam generating diodes have not been developed for UV lasers, should such a diode be developed it would be ideal for the present application. Any means for pulsating beam 12 would be useful for this application.

It is possible to combine the mirror scanning embodiment of the drawing with a precision optical translator, for example by scanning with one such technique in one dimension on the support and in a perpendicular direction with the other.

The term ultraviolet (UV) laser beam as used in this specification means lasers that emit in the UV at wavelengths preferable above 3200 Angstroms. Examples of lasers that emit in this region are Cadminum lasers (3250Å), Nitrogen lasers (3370Å), and Xenon Fluoride lasers (3520Å). Satisfactory lasers are those sold by LiCONiX Company of 3281 Scott Blvd. Santa Clara, Calif., 95054 such as HeCd Model No. 3207. Other models sold by this company are also satisfactory. A description of the technical details of these lasers may be found in U.S. Pat. Nos. 4,704,583 and 4,746,201.

A satisfactory precision translator is one manufactured by Oriel of 250 Long Beach Blvd., P.O. Box 872, Stratford, Ct. 06497, Model 16127 Standard Translator with 25 mm Motor Mike Drive.

The spinning mirror laser device depicted by the drawing is an adaptation of a laser printer such as is described and shown in the article "Lights? Camera? Print It? Laser Printer Technology Explained" by Alfred Poor (PC Magazine, Nov. 14, 1989, pp. 168–169).

The term "unit" as it is used in this specification shall mean chemical molecules or subdivisions thereof including radicals and reactive groups such as amino acids that may be linked together with other such molecules or subdivisions thereof to form chain compounds such as proteins.

The photolabile protecting groups may be any such group known in the art for use in conjunction with the chain compound being constructed. For example, in conjunction with the described polypeptides, amino groups at the ends of linkers attached to a glass substrata may be reacted with nitrovera-trioxycarbonyl (NVOC) a photoremovable protection group. The use of such compounds are described in a Research Article in the publication entitled "Light-Directed, Spatially Addressable Parallel Chemical Synthesis" by S. Fodor, et. al., Science, 251, 767 (1991).

As an example of the method of the present invention a LiCONiX UV laser Model 3207N may be used to provide a continuous 3250 Å UV laser beam to photoprotected amino acid units attached to a glass support. The components of this device are those illustrated in the drawing. Radiation of wavelength longer than 3200 Å will not affect even the most light sensitive amino acid, tryptophan. The rotating mirror and detector (UV enhanced silicon photodiode detector) are linked to a controller 28 through a detector 26 (available from H&N Instruments) to control the scan rate. Focusing of the beam is accomplished using fused silica laser lenses ("Best Form", Oriel) capable of producing spot sizes on the order of a few micrometers. The support 18 consists of a glass microscope slide contained in a small bath which is attached to a precision drive manual translator (Oriel) with 0.02 um resolution. A liquid chromatograph (Pharmacia "FPLC system") is programmed to react the glass support with the required solutions. The entire apparatus is assembled on a standard optical platform with vibration control (Kinetics Vibration Table). The protocol for peptide synthesis is similar to the procedures governed by Fodor, et. al. (Science, 251, 767 [1991]). These are as follows:

1. The glass slide is aminated by dipping it in a solution of 0.1% aminopropyltriethoxysilane in 95% ethanol, and curing at 110° C. for 20 minutes. Alternatively the solution may be methanol containing 0.1% each of aminopropyltriethoxysilane, a wetting agent (such as Pluronic L122, manufactured by BASF Corp.), water, and acetic acid, followed by curing at 140° C. for ten minutes.

2. Free amino sites are reacted with an in situ generated hydroxybenzotriazole (HOBt) ester of a nitroveratryloxycar-abonyl (NVOC) or 2-nitrobenzyloxycarbonyl (NBOC) amino-protected amino acid, such as NVOC-Leucine. These are formed by mixing 0.25 mmol of the NVOC amino acid with 37 mg HOBt, 111 mg of benzotriazolyl-n-oxy-tris(dimethylamino) phosphonium hexafluorophosphate (BOP), and 86 ul of diisopropylethylamine (DIEA) in 2.5 ml of DMF. The coupling takes 2 hours at room temperature.

3. The slide is washed with dimethylformamide (DMF) and methylene chloride. Supports about 0.1 mm high are placed around the edges of the slide, and a UV optical grade fused quartz window is placed on these supports. A solution of 1% semi-carbazide hydrochloride in a UV transparent solvent such as methanol or ethylene glycol is then injected onto the slide, filling the space between the slide and quartz window. A solution of semi-carbazide hydrochloride is necessary to make the subsequent photochemical reaction quantitative [see "Photoremovable Protecting Groups in Organic Synthesis", V. Pillai, Synthesis, 1 (1980), and A. Patchornik, et al., JACS, 92, 6333, (1970)]. The fused quartz window serves to guarantee a constant, optically reproducible quantity of solvent present during the subsequent deprotection step.

4. Deprotection is accomplished by scanning the laser described above over the programmed sites.

5. Steps 2–4 are repeated as required. In step 2 other NBOC or NOVC-amino acids are reacted as desired.

6. The entire surface is scanned at the end of the synthesis to photolyze the remaining NVOC or NBOC groups.

The first layer of immobilized amino acid serves to introduce a photolabile species into the array and is not varied. All other positions in the immobilized peptide can be varied.

A shutter may be added to generate spots and the glass support may be rotated to produce a grid.

A complete automation of the apparatus involving using a detector 26 and a central controller 28 to control the LC apparatus (pumps, valves) as well as the optical apparatus may be employed.

A significant advantage of the method of the present invention is the ability to completely automate the synthesis of immobilized peptide arrays. Automation can be efficiently accomplished using a H & N Instruments controller.

The H & N Instruments controller is based on the Mororola 68HC11 microcontroller with New Micros MaxForth. This microcontroller has 5 digital I/O 8 bit ports, 2 serial communication ports, 5 timers, 512 bytes of EEPROM, 256 bytes of RAM, and a Forth kernel in 8K of on chip ROM. These features are contained in a single 52 pin chip. H & N Instruments has designed circuit modules that combine with this chip to provide additional memory (EPROM or RAM), high resolution analog I/O, and control of 4 floppy disk drives. These modules are combined on a custom designed circuit boards, designed in-house using state-of-the-art CAD programs. The tools available in this hardware library are sufficient to implement most automation tasks.

The H & N Instruments controller is programmed in Forth for real time data collection and instrument control. Forth is an extensible high level programming language. It is easy to add options to the language. Every program written becomes an operation that can be used in the same manner as the operations that are native to the language. Every operation is a word which can be used along with other operations or words which can be used to define new words. Words or operations can be executed immediately by typing the word followed by a carriage return. The use of words to execute operations encourage modular programming. If the word itself describes the operation it performs, then it can be nearly self-documenting. Several words can be used to define program modules which then become words themselves-leading to a final program which is really a series of stacked program modules.

Forth is also a stacked oriented language. It uses post fix notation much like an HP calculator. The stack is extensively used and is especially useful for passing parameters from one part of a program to another. The stack eliminates the need for formal parameter of local variable declarations.

Forth is an interactive language. A word can be executed immediately after it is defined by typing the word followed by a carriage return. This feature is convenient for debugging and testing. A new word can easily be tested and modified until it works as desired. This is especially useful for debugging hardware control and I/0 interface programs.

H & N Instruments has a modular software library with routines for most common instrumentation and control tasks. It is analogous and complimentary to the hardware design library. Routines exist for floppy disk based data collection, temperature programming and control, analog voltage input and output, various timing functions, and a sophisticated user interface for inputing experiment and control parameters. These routines are programmed in Forth and are easily applied to the automation of the instant laser method.

As an example of the present invention utilizing the procedures set forth above, alternating rows of Gly (G) and γ-aminobutyric acid -Gly (GABA-G) are synthesized. The surface is incubated with rabbit anti-GABA antibody (available from Sigma Chemicals) which binds to GABA groups on the surface. A second incubation with gold conjugated goat anti-rabbit IGG is used to detect bound rabbit antibody. Development of the slide with silver stain yields alternating rows of light and dark bands, corresponding to bound Gly and GABA-Gly.

As another example (not yet completed) of the present invention utilizing the procedures set forth above alternating rows of $H_2N$-Tyr-Gly- Gly-Phe-Leu (YGGFL) and $H_2N$-Pro-Gly-Gly-Phe-Leu (PGGFL) are synthesized. The surface is reacted with mouse monoclonal antibody to β-endorphin (3E7-Accurate Chemical and Scientific Corp) which binds YGGFL and YGGFM. A second incubation with fluorescein-labeled goat antibody to mouse (Accurate Chemical and Scientific Corp) is used to detect bound 3E7. A high degree of binding of 3E7 to YGGFL rows only will demonstrate the fidelity of synthesis.

As a further example (not yet completed) of the present invention utilizing the procedures set forth above alternating rows of $H_2N$-Phe- Arg-Leu-Pro-Leu(FRLPL) , $H_2N$-Leu-Leu-Leu-Pro-Leu(LLLPL) , and $H_2N$-Phe-Arg-Met-Phe-Leu(FRMFL) are synthesized. The surface is reacted with fluorescein labeled polyclonal antibody to FRLPL (Peninsula Laboratory). This antibody binds FRLPL with a cross reactivity of 22% to FRMF. A high degree of binding of the antibody to FRLPL rows, weaker binding to FRMFL rows, and no binding to LLLPL rows will demonstrate the fidelity of synthesis.

Publications other than those mentioned above that may be helpful in understanding the invention are:

"Binding activities of a repertoire of single immunoglobulin variable domains secreted from Escherichia coli" E. S. Ward, et.al., Nature, Vol. 341, 544 (1989);

"Peptides, Structure and Function", edited by C. M. Deber, V. J. Hruby, and K. D. Kopple, Pierce Chemical Co., Rockford, Ill., (1985);

"Searching for Peptide Ligands with an Epitope Library" J. K. Scott and G. P. Smith, Science, Vol. 249, 386 (1990);

"Random Peptide Libraries: A Source of Specific Protein Binding Molecules" J. J. Devlin, L. C. Panganiban, and P. E. Devlin, Science, Vol. 249, 404 (1990);

"Laser Recording And Image-Quality Evaluation" K. Minoura, et.al., SPIE, Vol. 1254, 24 (1990);

"A laser scanning optical system for high-resolution laser printer" T. Maruyama, et.al., SPIE, Vol. 1254, 54 (1990);

"Immunogenicity of Synthetic Peptides Corresponding to Flexible and Antibody-accessible Segments of Mouse Lactate Dehydrogenase(LDH)-$C_4$*" H. Hogrefe, P. Kaumaya, and E. Goldberg, J. Biol. Chem., Vol. 264, 10513 (1989);

"Peptide engineering of protein topographic determinants for vaccines" P. Kaumaya, et.al., in "Peptides 1990", ESCOM Science B.V. (1991); and "Synthesis and Biophysical Characterization of Engineered Topographic Immunogenic Determinants with $\alpha\alpha$ Topology" P. Kaumaya, et.al., Biochemistry, 29, 13 (1990).

Having thus described the apparatus and procedural steps for carrying out the invention, it will be clear to those having ordinary skill in the art, that various modifications may be made in the apparatus and the procedural steps without departing from the inventive concept. It is not intended that the words used in the specification to describe the invention, nor the drawings illustrating the same, be limiting on the invention. Rather it is intended that the invention be limited only by the scope of the appended claims.

I claim:

1. In the process of making chemical compounds wherein photoprotected chemical units attached to the surface of a support are selectively irradiated to deprotect preselected areas of said surface so that the surface of said support may be subjected to chemical reaction disposed to attach chemical units to the deprotected units, the improvement in combination therewith of irradiating said surface with the laser beam of a laser printer, said laser having a wave length in the ultraviolet range.

2. The process of claim 1 wherein the chemical units attached to the deprotected units are photoprotected for subsequent irradiation with said laser beam.

3. The process of claim 2 wherein said units are subsequently irradiated with said laser beam and subjected to chemical reaction disposed to attach a chemical unit to the deprotected units.

4. The process of claim 3 wherein the steps of photoprotection of said units, irradiation and chemical reaction to attach a chemical unit to the deprotected units are repeated to achieve multichain chemical compounds.

5. The process of claim 1 wherein said laser beam is caused to scan said surface so as to effect parallel lines of deprotected areas.

6. The process of claim 5 wherein said laser beam is caused to pulsate on and off so as to effect individual restricted areas of deprotection.

7. The process of claim 5 wherein said support is rotated subsequent to such scan from 0 to 90 degrees to cause said lines to intersect.

8. The process of claim 1 wherein said laser beam wavelengths are above 3200 Angstroms.

9. The process of claim 1 wherein said laser beam printer comprises a laser beam directed onto the surface of a multisurfaced rotating mirror positioned so that each mirror surface reflects said beam onto said surface to scan said surface.

10. The process of claim 2 wherein the chemical units attached to said support are amines and the chemical units attached to the deprotected areas are amino acids.

11. The process of claim 3 wherein the chemical units attached to said support are amines and the chemical units subsequently attached to deprotected units are amino acids so that the linkage between the units are peptide linkages.

12. The process of claim 4 wherein the chemical units attached to said support are amines and the chemical units subsequently attached to deprotected units are amino acids so that the linkage between the units are peptide linkages.

* * * * *